United States Patent [19]
Goble et al.

[11] Patent Number: 6,074,386
[45] Date of Patent: *Jun. 13, 2000

[54] ELECTROSURGICAL INSTRUMENT AND AN ELECTROSURGICAL ELECTRODE ASSEMBLY

[75] Inventors: Nigel Mark Goble, Cardiff; Colin Charles Owen Goble, Penarth, both of United Kingdom

[73] Assignee: Gyrus Medical Limited, Cardiff, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/907,262

[22] Filed: Aug. 6, 1997

Related U.S. Application Data

[63] Continuation of application No. 08/677,128, Jul. 9, 1996, abandoned.

[30] Foreign Application Priority Data

| Dec. 29, 1995 | [GB] | United Kingdom | .................... 9526627 |
| May 3, 1996 | [GB] | United Kingdom | .................... 9609280 |

[51] Int. Cl.[7] .................................................. A61B 17/36
[52] U.S. Cl. ............................................. 606/34; 606/42
[58] Field of Search ................................. 606/32–35, 38, 606/41–42, 72

[56] References Cited

U.S. PATENT DOCUMENTS

| 4,200,104 | 4/1980 | Harris ......................................... 606/32 |
| 4,580,557 | 4/1986 | Hertzmann ................................ 606/12 |
| 5,575,789 | 11/1996 | Bell et al. .................................. 606/42 |

FOREIGN PATENT DOCUMENTS

| WO 94/10921 | 11/1993 | European Pat. Off. . |
| 3427517 A1 | 1/1986 | Germany . |
| 4339049 A1 | 5/1995 | Germany . |
| 1361497 | 7/1974 | United Kingdom . |

*Primary Examiner*—William E. Kamm
*Attorney, Agent, or Firm*—Nixon & Vanderhye, P.C.

[57] ABSTRACT

An electrosurgical instrument primarily intended for so-called "underwater" electrosurgery has a radio frequency generator, a handpiece, and an electrode assembly detachably mounted to the handpiece. Different electrode assemblies may be selected according to the surgical procedure to be performed. To adapt the generator characteristics for improved electrosurgical performance, each electrode assembly contains an identification element such as a capacitor of unique value which is sensed by the generator. Inside the generator, the sensed capacitor value causes the selection of operating parameters, preferably a nominal generator output power and a peak voltage limit, to suit the selected electrode assembly.

35 Claims, 5 Drawing Sheets

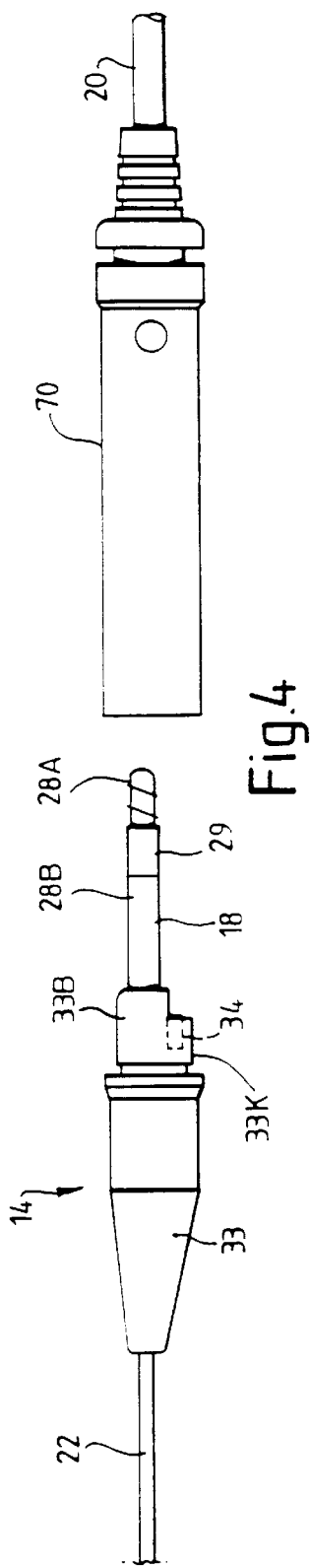
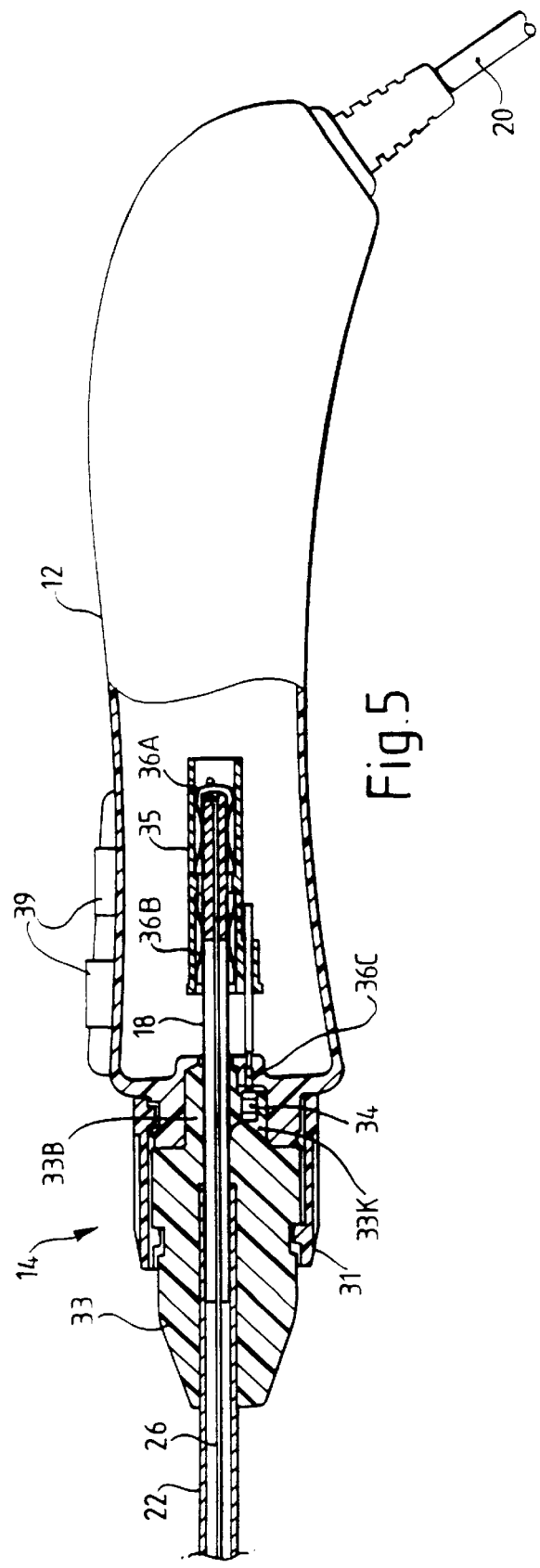

6,074,386

ELECTROSURGICAL INSTRUMENT AND AN ELECTROSURGICAL ELECTRODE ASSEMBLY

This is a continuation of application Ser. No. 08/677,128 filed Jul. 9, 1996, now abandoned.

FIELD OF THE INVENTION

This invention relates to an electrosurgical instrument having a generator for generating radio frequency power, a handpiece, and a detachable electrode assembly. The invention also includes an electrode assembly for detachable mounting to a handpiece of an electrosurgical instrument, a method of assembling and operating the instrument, and an electrosurgical generator.

BACKGROUND OF THE INVENTION

Surgery by the application of radio frequency currents to living tissue to desiccate, cut, or vaporise the tissue using one or more electrodes coupled to a radio frequency generator raises particular problems in terms of obtaining efficient transfer of power from the generator to the tissue and producing a required surgical effect in a controllable manner. The electrical characteristics of an electrode assembly when in use can vary widely depending on the mode of use, the conductivity of the tissue and surrounding substances, and the nature of the assembly itself.

These problems are particularly evident in the case of electrosurgery performed with an electrode or electrodes immersed in liquid at the operation site (often referred to as "underwater" electrosurgery).

Underwater surgery is commonly performed using endoscopic techniques in which (1) the endoscope itself may provide a conduit for passage of an electrode, commonly referred to as a working channel, or (2) the endoscope may be specifically adapted to include means for mounting an electrode, such as are provided on a resectoscope, or (3) the electrode may be introduced to the body cavity via separate access means at an angle with respect to the endoscope; a technique commonly referred to as triangulation. These variations in technique can be subdivided by surgical speciality, where one or other of the techniques has particular advantages given the access route to the specific body cavity. Endoscopes with integral working channels or those characterised as resectoscopes, are generally employed when access to the body cavity may be through a natural body opening; such as the cervical canal to gain access to the endometrial cavity of the uterus or the urethra to gain access to the prostate gland and bladder. Endoscopes specifically designed for use in the endometrial cavity are referred to as hysteroscopes. Those for the urinary tract include cystoscopes, urethroscopes and resectoscopes used during transurethral resection or vaporisation of the prostate gland (TURP and EVAP, respectively). When there is no natural body opening through which the endoscope may be passed, the technique of triangulation is commonly employed. A common site where triangulation is used is during underwater endoscopic surgery on joint cavities such as the knee and shoulder. The endoscope used in these procedures is commonly referred to as an arthroscope.

In our co-pending British Patent Applications Nos. 9512888.0 and 9512889.8 (the disclosure of which is incorporated herein by reference) we disclose an electrosurgical generator and an electrode assembly designed for operation with electrodes immersed in a conductive liquid such as saline solution. The electrode assembly has two electrodes; a first, active electrode at the extreme distal end of the assembly for contacting the tissue to be treated, and a second, return electrode spaced proximally from the active electrode and separated from the latter by an insulation barrier. When the electrodes are immersed in the saline solution, the solution provides a conductive path between the tissue next to the active electrode and the proximal return electrode which remains spaced from the tissue. The electrode assembly is fed by a generator which includes a rapid-acting power reduction circuit operating to prevent significant vapour formation at the active electrode during electrosurgical desiccation. The output power supplied to the electrode assembly by the generator is rapidly reduced when the peak output voltage reaches a preset threshold with the object of avoiding a rapid runaway increase in power delivery and arcing when vaporisation commences, which would lead to uncontrollable tissue disruption in place of the required desiccation. This effect is especially problematical when the generator has a significant output impedance. Different electrode assemblies can be used to perform different electrosurgical functions.

It is an object of the present invention to provide an electrosurgical instrument which produces a controllable surgical effect and which is versatile in use.

SUMMARY OF THE INVENTION

According to a first aspect of this invention there is a provided an electrosurgical instrument comprising a first unit including a generator for generating radio frequency power, and a second unit including an electrode assembly, the second unit being detachably connectible to the first unit such that radio frequency power can be conveyed to the electrode assembly, wherein the second unit includes a passive electrical identification component having a parameter of a finite non-zero value indicative of a characteristic of the electrode assembly, and the first unit includes sensing means for sensing the parameter value when the second unit is connected to the first unit, the generator including adjustment means responsive to the sensing means to adjust the output of the generator so as to suit the indicated electrode assembly characteristic. In this way the generator can be configured automatically to suit a variety of different electrode assemblies so that the same generator can be used for different electrosurgical operations, the operator being relieved of much of the task of setting the generator to suit the selected electrode assembly.

This is particularly useful in the case of so-called underwater electrosurgery as described above and in the above-mentioned co-pending applications. The applicants have found that the power levels which can be applied whilst performing desiccation vary widely depending on the construction of the electrode assembly. By including in each electrode assembly an identification component which is indicative of, for example, a vaporisation power threshold of the assembly, this characteristic of the assembly can be communicated to the generator so that the radio frequency output can be set accordingly. Thus, improved control, particularly in desiccation operations, can be achieved whilst maintaining the ability to use different electrode assemblies with the same generator. For cutting and tissue vaporisation, vaporisation of the immersion liquid is required, but the power level applied should not exceed that which causes damage to the electrode assembly. It is possible to use the present invention to set a radio frequency voltage limit so as to limit the extent of tissue vaporisation to avoid exceeding the power rating of the electrode assembly.

The first unit may comprise the generator, a connector (which may be integrated into an instrument handpiece), and a cable for coupling the generator to the connector. In this case the second unit may be constituted by the electrode assembly, which assembly itself has a connector which mates with the connectors of the first unit, thereby providing a demountable mechanical interface.

Alternatively, the first unit may comprise a generator with a first connector, while the second unit comprises the combination of the electrode assembly, a second connector, and a cable connecting the second connector with the electrode assembly, so that the mechanical interface is provided on the generator. In this case, the electrode assembly may be detachably or non-detachably mounted in a handpiece or a housing forming part of the second unit.

In both configurations, the mechanical interface may provide further means for controlling or adjusting the generator according to the component connected to it. In particular, the interface may comprise a specific plug and socket combination in which both the plug and the socket are shaped such that neither can be used with a different socket or plug respectively. Consequently different plug and socket combinations can be provided for different surgical applications. For instance, a first combination may be used for hysteroscopic system, another one for arthroscopic applications, and so on.

Accordingly, if the generator has a socket of a type which is designated for, say, hysteroscopic procedures, the generator circuitry is arranged to supply output signals to that socket which are suited to such procedures. If, on the other hand, the generator has a socket of a type designated for arthroscopic procedures, the generator circuitry supplies signals to that socket which are more suited to arthroscopic procedures. A range of electrode assemblies may be provided for each class of procedures, and the generator can be configured such that the electrical identification components in the electrode assemblies for one class of procedures affects the generator output differently from the same group of identification components when used in electrode assemblies for a different class of procedures. In effect, the generator is configured to provide signals which are adjustable in response to the identification component according to the type of socket to which the output signals are supplied. In this way, the available range of different signal outputs is expanded beyond that available by simply adjusting the output according to the value of the identification component.

It is in this light that the preferred instrument in accordance with the invention provides a mechanical interface between the first and second units which is formed of a plug and a socket having respective interfitting configurations selected from a range of different shapes so that the first and second units are operable together only if they have such interfitting plug and socket shapes.

More specifically, in a preferred electrosurgical instrument in accordance with the invention, the first unit includes an output connector for delivering output signals to the second unit, the configuration of the output connector being specific to the field of the surgery for which the output signals are suited. The second unit has an input connector for receiving the output signals from the generator and supplying them to the electrode assembly, the configuration of the input connector being specific to the field of surgery for which the electrode assembly is suited. The configurations of the input and the output connectors form an interfitting combination such that the electrode assembly and the generator are interoperable only when both the electrode assembly and the output signals applied to the said connector are suited to the same field of surgery.

The manner in which the sensing means and the adjustment means respond to the identification component is dependent on the configuration of the said output connector. As a result, the electrode configurations and the respective electrosurgical output can be optimised depending on the type of endoscope, and hence the type of surgical procedure, being used. The system, comprising specific electrode assemblies, the generator, and connector means between the electrosurgical generator and a selected electrode assembly, can be categorised as an arthroscopic system, a hysteroscopic system or an endoscopic urological system, using a unique cable/plug assembly for each of the speciality segments.

The arthroscopic electrodes may be characterised as short (100–140 mm), rigid with a working diameter up to 4 mm. They are introduced through a stab incision into the joint cavity with or without a cannula using the triangulation technique. The tissue to be treated is commonly dense and of high electrical impedance, such as meniscal cartilage. Output power and voltage settings reflect both the type of tissue, the size of electrode and the fact that arthroscopists are seeking a speed of effect comparable to the mechanical shaver devices they current employ, albeit from an electrode of smaller diameter than shaver blades to improve access. Arthroscopic electrode assembly designs therefore need to support relatively high output specifications, produce rapid debulking of high impedance tissue and must connect to an ergonomic handpiece to aid tissue manipulation. In the arthroscopic system, then, the range of electrode assembly identifications are subdivided to arthroscopic electrode assembly identification and generator system set-up settings according to these specifications and surgical techniques.

The hysteroscopic electrodes may be characterised as long (350–400 mm), flexible or semi-rigid, and with a working diameter typically in the range of 1.27–2.86 mm (4–9 Fr). They are introduced through a working channel. The tissue is commonly more vascular than that encountered during arthroscopic surgery and inadvertent perforation of the uterus represents a serious complication. It is desirable therefore to support a more controlled application using electrodes with good desiccation capability using more precise movement of the electrode or hysteroscope than is normal during arthroscopic procedures. The electrode assembly to generator interface does not require a true "handpiece" and may merely constitute connector means. In the hysteroscopic system, the range of electrode identifications are, therefore, differently subdivided to hysteroscopic electrode identification and generator system set-up settings according to these specifications and surgical techniques.

There are two main electrode configurations for endoscopic urological procedures: (1), cystoscopic/urethroscopic electrode, and; (2), resectoscope electrodes. The former have characteristics very similar to the hysteroscopic electrode, being introduced through the working channel of urological endoscopes. Resectoscope electrodes are introduced very differently, in that they are mounted on an endoscope prior to passage of the assembled instrument through a working sheath introduced via the urethra. The proximal end of the electrode is connected to a trigger assembly and electrical contact integral to the resectoscope. By this means, the electrode can be moved back and forth through a defined range of motion by operating the trigger mechanism. As the electrode is assembled prior to introduction, the size of the tip is not constrained by working channel dimensions but rather by the working sheath. The working sheath diameter can range up to 10 mm. Part of this diameter is occupied by the support wires to the electrode which are commonly bent in a downward angle, with respect to the endoscopic image, to the working tip so that they do not interfere with either visualisation or its operation. Nonetheless, a typical roller electrode may be in the range of 3–4 mm wide and 2–3 mm in diameter. This size is necessary given that, on average, 20–30 grams of prostate tissue must be removed. The tissue is of variable consistency as a mixture of fibrous and glandular elements, areas of which may be quite vascular. A combination effect of simultaneous desiccation and vaporisation is, therefore, required. The roller form of urological electrode requires a high power high voltage generator output. In the urological system, the range of electrode identifications are, therefore, subdivided to a further group of urological endoscopic electrode assembly identification and system set-up settings according to these specifications and surgical techniques.

In addition to segmentation of electrode assembly identification to the above underwater surgical specialities, further subdivision of generator settings may be included for electrode assemblies designed for operation in a saline working environment confined to the tip of the electrode. As such, this electrode assembly design significantly increases the system versatility in surgical procedures either performed in open air or under a gaseous distension. The former may be performed under direct vision to debulk, incise or coagulate a tissue mass or by a triangulated endoscopic approach such as those performed to remove spinal disc herniations or to remove diseased tissue from the sinuses; so-called functional endoscopic sinus surgery. Examples of gaseous distension techniques include laparoscopic and gastrointestinal endoscopic surgery. The range of electrode identifications are, therefore, subdivided to yet a further group of saline assisted electrode identification and system set-up settings according to these specifications and surgical techniques.

In the above variations on the invention from the complete instrument aspect have been described. Other aspects of the invention are now introduced. It will be understood that the above-described variations apply similarly.

According to a second aspect of the invention, an electrode assembly for an electrosurgical instrument, the assembly comprising at least one electrode mounting means for detachably mounting the assembly to an another part of the instrument, and a passive electrical identification component arranged to interact with sensing means associated with said other part of the instrument, the identification element having a parameter of a finite non-zero value indicative of the assembly.

The identification element is preferably a passive component of predetermined impedance such as a discrete capacitor, the impedance being indicative of the above-mentioned electrode assembly characteristic. Preferably, in the case of the component being a capacitor, the capacitor value varies from electrode assembly to electrode assembly in the range of, typically, 15 pF to 1 $\mu$F according to a power level threshold for the assembly. In the case of an electrode assembly intended for use in an immersing liquid, the threshold may be that at which vaporisation normally occurs, preferably with the capacitance values increasing with increasing power threshold value.

The electrode assembly mounting means may include at least a pair of electrical contacts arranged to engage electrical contacts in an instrument handpiece, the capacitor being connected between the contacts of the electrode assembly so that when the assembly is mounted to the handpiece, the contacts engage correspondingly located contacts on the handpiece which are connected to the sensing circuit in the generator.

In the preferred embodiment, the identification component is coupled between an identification contact and a contact which serves for the conduction of radio frequency currents between the generator and the electrode assembly. In a bipolar instrument there are typically three contacts, two for the conduction of radio frequency currents and one for identification of the electrode assembly. A single identification contact arrangement allows identification of three or more different electrode assemblies, depending on the number of different identification parameter values used in the system and which the generator sensing means is capable of distinguishing.

With respect to the generator, according to a third aspect of the invention, an electrosurgical generator for use with a plurality of different electrode assemblies including respective electrical identification components having different finite non-zero parameter values indicative of the characteristics of the electrode assemblies, wherein the generator includes sensing means responsive to the parameter values and means for automatically setting the output of the generator according to the indicated characteristic of an electrode assembly connected to the generator.

In a preferred embodiment, the identification component is a capacitor and the sensing means includes a reactive component in the form of an inductance which forms a resonant circuit with the identification capacitor when the electrode assembly is connected to the generator, the resonant frequency of the resonant circuit being dependent on the value of the capacitor. The sensing means may also include an oscillating device for example a suitably connected transistor, with the resonant circuit forming part of a self-oscillating circuit so that the oscillator frequency is determined as the resonant frequency of the resonant circuit. In this case, the oscillator frequency is indicative of the electrode assembly characteristic.

Alternatively, the sensing means may include a variable internal capacitance or inductance, with means for switching in different inductance or capacitance values, or for varying the inductance or capacitance value until a combination which is resonant at a predetermined fixed frequency is found.

The inductance in the sensing means may comprise a first winding of an isolation transformer, this winding being connected between a pair of contacts in a connector or an instrument handpiece which engage contacts on the electrode assembly bridged by the identification capacitor so as to form the resonant circuit when the electrode assembly is connected to the generator. A second winding of the transformer preferably forms part of the oscillator, typically in the form of a sensing winding for providing feedback to the oscillator device. The transformer may have a third, excitation winding coupled to the output of the oscillating device. Alternatively, a second transformer may be provided, this having a first winding coupled to the output of the oscillating device to act as an excitation winding, and a second winding coupled in series in the resonant circuit formed when the electrode assembly is connected to the generator. In this case, two transformer windings, one from each transformer, constitute the inductance which resonates with the identification capacitor in the electrode assembly.

In an electrode assembly having an active electrode and a return electrode as described above, the electrode assembly identification function may be achieved with three electrical contacts by connecting the active electrode to one contact, the return electrode to another contact, and the capacitor to the third contact, with the other terminal of the capacitor connected to one of the contacts assigned to the electrodes. The capacitor may be quite small and mounted immediately distally of the contacts in a contact housing which is shaped to be received on or in a connector or handpiece which is, in turn, connected to the generator.

In the generator, the sensing means may be coupled to adjustment means in the form of a controller which is arranged to set the output power of the generator according to an output signal provided by the sensing means and representative of the identification characteristic. The controller is preferably operable to adjust the average supply voltage supplied to a radio frequency output circuit (in this case a power oscillator) in response to the sensing means output signal. In the case of the generator including a switched mode power supply, the controller is coupled to the power supply and arranged to adjust the duty cycle of the switched output of the power supply in response to the sensing means output signal.

The invention is applicable to instruments in which the generator is separate from an instrument handpiece or incorporated in the handpiece. The sensing means may be incorporated in the handpiece whether or not the generator is also in the handpiece.

According to a fourth aspect of the invention there is provided a method of assembling and operating an electrosurgical instrument comprising: providing a first unit including an electrosurgical generator for generating radio frequency power; providing a plurality of second units comprising different electrode assemblies each having means for detachable mounting to the first unit and each including an electrical identification component having a parameter of a finite non-zero value indicative of a characteristic of the respective assembly; selecting one of the second units and mounting it to the first unit; and in the first unit, sensing the identification component parameter value and automatically adjusting the generator output in response to said sensing to suit the characteristic of the electrode assembly of the selected second unit.

The invention includes, according to a fifth aspect thereof, a kit of parts for assembling an electrosurgical instrument, comprising a first unit including an electrosurgical generator for generating a radio frequency electrosurgical voltage, and a plurality of different second units including different electrode assemblies, each second unit including means for mounting to the first unit, wherein each second unit includes an electrical identification component having a parameter of a respective value selected from a range of finite non-zero values and indicative of a characteristic of the respective electrode assembly, and the first unit includes means for sensing the indicating parameter when the second unit is mounted to the first unit, the generator including adjustment means responsive to the sensing means to adjust the output of the generator, whereby the generator output is automatically adjusted to suit the different characteristics of the electrode assemblies of the second units when they are selectively mounted to the housing according to the sensed parameter value.

BRIEF DESCRIPTION OF THE DRAWINGS

The drawings illustrate preferred embodiments of the invention which we give by way of example only. In the drawings:

FIG. 4 is a side elevation of an electrode assembly and connector unit of an electrosurgical instrument for hysteroscopic procedures, the electrode assembly and connector unit being shown prior to the attachment of one to the other;

FIG. 5 is a partly sectioned side view of an electrode assembly and handpiece for an electrosurgical instrument for arthroscopic procedures.

DETAILED DESCRIPTION OF THE PREFERRED EMBODIMENTS

Figures 1, 1A:
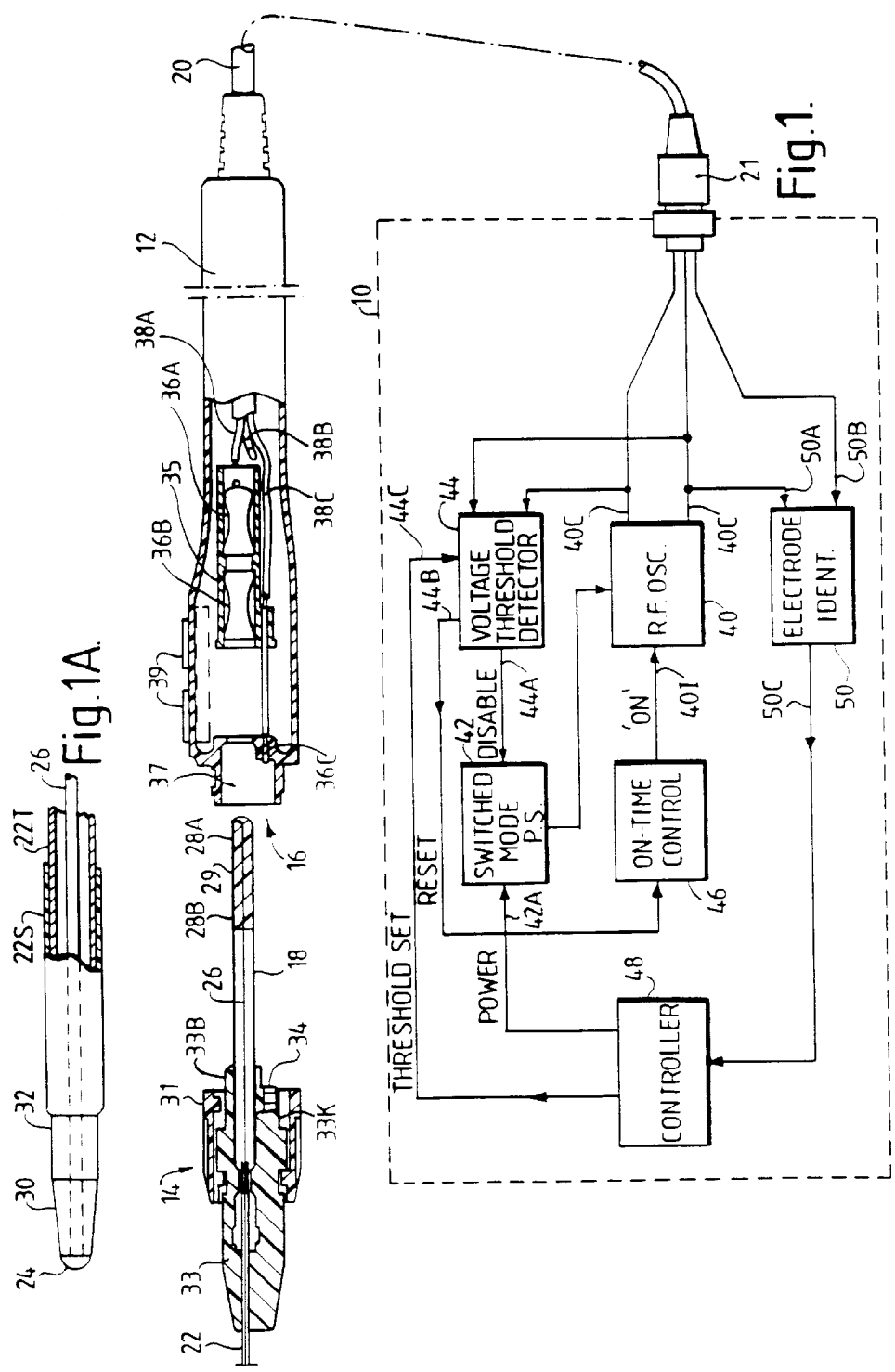
FIG. 1 is a diagrammatic representation of an electrosurgical instrument for urological procedures, in particular cystoscopic procedures, in which an electrode assembly and handpiece are shown partly in cross-section, and a generator is shown in block diagram form.
FIG. 1A is a detail view showing the distal tip of the electrode assembly in FIG. 1, partly in longitudinal cross-section.

Referring to FIGS. 1 and 1A, an electrosurgical instrument in accordance with the invention comprises a generator 10 for generating radio frequency power, a pencil-grip handpiece 12, shown partly sectioned in FIG. 1, and a detachable electrode assembly 14, shown detached from the handpiece 12 in FIG. 1, but aligned with an aperture 16 of the handpiece, which receives a plug section 18 of the electrode assembly 14. In this embodiment of the invention, the generator 10 is separate from the handpiece 12, the two being connected by a cable 20 and an output connector 21, as shown.

The electrode assembly is of a construction generally described in our co-pending British Patent Application No. 9512889.8. In FIG. 1, the distal end of the assembly is not shown, but appears in FIG. 1A to a larger scale. The assembly has a shaft 22 in the form of a conductive tube 22T covered with an insulating sheath 22S. At the extreme distal end of the shaft 22 there is an exposed central tissue contact or active electrode 24. This is a hemispherical metallic tip connected to a metallic wire which extends as a central conductor 26 through the whole of the shaft to a first contact 28A on the plug section 18 at the proximal end of the assembly 14. Surrounding the central electrode 24 is an insulating sleeve 30, the distal end of which is exposed proximally of the exposed part of the active electrode 24. Surrounding the sleeve 16 is a coaxial return electrode 32 in the form of a metallic tube which is electrically and mechanically integral with a metallic tubular body 22T of the shaft 22. The return electrode 32 is connected to a second contact 28B on the plug section 18 of the electrode assembly 14. In order that it is both radially and axially spaced from the active electrode 24, the return electrode 32 terminates at a point short of the end of the sleeve 30. In normal circumstances, only the active electrode 24 contacts the tissue to be treated; the return electrode 32 is immersed in an electrically conductive solution such as saline solution so that an electrical conducting path is formed between the tissue surrounding the active electrode 24 and the return electrode 32.

The electrode assembly plug section 18 is secured in a plastics housing 33 which also supports the shaft 22. This housing has a boss 33B coaxially surrounding the plug section 18, and a laterally projecting key portion 33K. A rotatable bayonet ring 31 secures the housing 33 to the handpiece 12.

The housing 33 contains a discrete passive electronic component, in this case in the form of a small capacitor 34 one terminal of which is connected to the conductive tube 22T and the other terminal of which forms a third contact exposed on the proximal surface of the housing key portion 33K.

When the electrode assembly 14 is attached to the handpiece 12, the plug section 18 passes through aperture 16 and into an inner housing 35 which has spring electrical contacts 36A, 36B arranged to engage contacts 28A and 28B of the electrode assembly plug section 18. Associated with aperture 16 is a recess shaped to match the outer profile of boss 33B and key portion 33K of the electrode assembly housing 33, and a third electrical contact 33C, which is spring-loaded, is located in the recess 37 to engage the exposed terminal of capacitor 34.

Each of the three contacts 36A to 36C is connected in the handpiece 12 to respective conductors 38A, 38B, 38C of the cable 20. In this case, cable 20 has two further conductors (not shown) for connection to push-button switches 39 located in the handpiece body.

Several different electrode assembles may be provided, each having a plug section 18 and a housing 33 which fits the handpiece 12, and each having an identification element (capacitor 34) the value of which is unique to the respective electrode assembly so that the capacitance between contacts 28A and the exposed terminal of capacitor 34 identifies the respective electrode assembly. Preferred examples of different electrode assemblies are the subject of co-pending British Patent Applications Nos. 9600352.0, 9600354.6, 9600355.3, 9600356.1 and 9600377.7, the contents of which are incorporated herein by reference.

The cable 20 is connected to the generator 10 by means of a generator output connector assembly 21 which is unique to the category of surgical procedures for which the generator output is intended, in this case urological procedures.

Referring now to the elements of the generator 10 as shown in FIG. 1, a radio frequency (RF) power oscillator 40 has a pair of output connections 40C coupled to conductors 38A and 38B of cable 20 via connector 21, and thence to the active and return electrodes 24, 32 respectively of the electrode assembly 14. Power is suppled to the oscillator by a switched mode power supply 42 coupled to the oscillator 40. In the preferred embodiment, the oscillator 40 operates at about 400 kHz, with any frequency from 300 kHz upwards into the HF range being feasible. The switched mode power supply typically operates at a frequency in the range of from 25 to 50 kHz. Coupled across the output connections 40C is a voltage threshold detector 44 having a first output 44A coupled to the switched mode power supply 42 and a second output 44B coupled to an on-time control portion 46 of a control circuit. Another, controller part 48 of the control circuit, preferably configured in the form of a microprocessor controller coupled to operator controls and a display (not shown), is connected to a control input 42A of the power supply 42 and to a threshold-set input 44C of the voltage threshold detector 44.

The "on" time control circuit 46 is coupled to the RF oscillator 40 to control the period of conduction of the oscillating output device of the oscillator 40 in each cycle of radio frequency oscillation, thereby to control the power delivered to the electrode assembly 14.

The generator 10 also includes an electrode identification circuit 50 having input terminals 50A and SOB connected respectively to contacts 36B and 36C of the handpiece 12 so that the capacitor 34 in the electrode assembly, when mounted in the handpiece 12, is connected across the inputs to the electrode identification circuit 50. This circuit 50 has an output 50C coupled to an input of the controller 48.

In operation, the controller 48 causes power to be applied to oscillator 50 by the switched mode power supply 42 when electrosurgical power is demanded by the surgeon operating one of the activation switches 39 on the handpiece 12. An output voltage threshold is set via input 44C according to control settings on the front panel (not shown) of the generator 10. Typically, for desiccation, the threshold is set at a desiccation threshold value between 150 volts and 200 volts. When a cutting or vaporising output is required, the threshold is set to a value in the range of from 250 volts to 600 volts, the value being dependent on the value of the capacitor 34 in the electrode assembly 14, as represented by the output signal produced by the electrode identification circuit 50 on output 50C. The voltage values given above are peak values. The fact that they are peak values means that for desiccation at least, it is preferable to have an output radio frequency waveform of low crest factor to give maximum power before the voltage is clamped at the values given. Typically a crest factor of 1.5 or less is achieved.

When the generator is first activated, the status of the control input 401 of the oscillator 40, which is connected to the "on" time control part 46 of the control circuitry, is "on", such that the power switching device which forms the oscillating element of the oscillator 40 is switched on for a maximum conduction period during each oscillation cycle. The power delivered to the electrode assembly 14 depends partly on the supply voltage applied to the RF oscillator 40 from the switched mode power supply 42 and partly on the load impedance. The switched mode power supply 42 produces a supply voltage which is dependent on the "power" signal applied at its input 42A by the controller 48 which, in turn, depends on the front panel settings and the value of the capacitor 34 in the selected electrode assembly 14.

If the supply voltage applied to the oscillator 40 by the switched mode power supply 42 is sufficiently high, the temperature of the liquid medium surrounding the electrodes 24 and 32 may rise to an extent such that it vaporises, leading to a rapid increase in load impedance and a consequent rapid increase in the applied output voltage across the terminals 40C of the oscillator 40. This is an undesirable state of affairs if a desiccation output is required. For this reason, the threshold voltage for a desiccation output is set to cause trigger signals to be sent to the "on" time control circuit 46 and to the switched mode power supply 42 when the threshold is reached. The "on" time control circuit 46 has the effect of virtually instantaneously reducing the "on" time of the RF oscillator switching device, and simultaneously the switched mode power supply is disabled via output 44A of the detector 44 so that the voltage supplied to the oscillator 40 begins to fall.

Subsequently, the "on" time of the individual cycles of the oscillator 10 is progressively increased until the output voltage threshold is once again breached, causing a further instantaneous reduction in "on" time. As the supply voltage is reducing, the period during which the oscillator "on" time is reduced can be shortened for a given delivered output power so that, if necessary, further instantaneous power reductions can be obtained in the same way as described above. The manner in which this process is achieved is described in the above-mentioned British Patent Application No. 9512888.0.

The operation of the control circuit 46, 48 so as dynamically to control the output voltage sufficiently rapidly and to a sufficient degree to maintain the delivered power at a level suitable for desiccation can also be used in tissue cutting or vaporisation mode with a different threshold voltage dynamically to limit the output voltage to prevent electrode burning and/or excessive tissue vaporisation. In this latter case, the voltage limit may be set to a level between 250 volts and 600 volts depending on the value of capacitor 34 (FIG. 1).

Both the initial power level of the RF oscillator 40 and the threshold voltage in the vaporisation mode can be adjusted according to the value of the capacitor 34 in the electrode assembly 14 using the electrode identification circuit 50 and adjustment means in the controller 48. Thus, voltage overshoot and consequent unwanted vaporisation in the desiccation mode can more easily be avoided. This is of particular concern when sealing blood vessels by desiccation, prior to cutting or vaporisation. Similarly, in the vaporisation mode, a nominal power level can automatically be set according to the electrode assembly so as to deliver a minimum power level necessary to achieve vaporisation. Also in the vaporisation mode, the maximum voltage level can be set, thereby determining the size of the vapour pocket created by the particular electrode assembly connected to the handpiece. The size of the vapour pocket in turn determines the amount of tissue removed adjacent the electrodes. Higher operating voltages, however, cause higher active electrode temperatures. Thus, if the active electrode is made of a noble metal, it is capable of withstanding a higher voltage than one constructed of less robust materials. In such circumstances, the electrode may be excessively eroded or melted, and the capacitor 34 can be used to set the voltage threshold detector in the vaporisation mode to prevent this.

With regard to adjusting the oscillator power level, the capacitor 34 is used to communicate the identity of the electrode assembly, and thus an appropriate power level, to the generator for the respective electrode assembly 14. The generator may typically have a maximum power level of 200 watts, and the minimum power level required for vaporisation for the assembly may be as low as 30 watts. To achieve an approximately logarithmic division of power levels to suit different electrode assemblies, different capacitor values can be used to represent power levels such as 30, 45, 70, 100, and 150 watts. An alternative logarithmic division is 30, 42, 58, 80, 110, and 150 watts. Capacitor values between 15 pF and 1 µF can be used to indicate these power levels. If these values correspond to power thresholds, then for the desiccation mode the controller is arranged to set powers slightly below the respective values, while for vaporisation, the set values are slightly higher.

The voltage maximum for vaporisation may also be communicated, if necessary, by using further capacitor values or by including a second identification element in the electrode assembly and a fourth set of contacts and an additional conductor in the cable 20.

It is preferred that the greater the nominal power rating of the electrode assembly, the greater is the value of the capacitor 34. This allows for the possibility of failure of the electrode identification parts of the instrument, with the generator defaulting to the least power and voltage setting for safety reasons.

One benefit of setting a nominal power level according to the electrode assembly attached to the handpiece is that power can be supplied to the assembly immediately at the nominal level rather than being increased progressively to that level when the electrodes are first applied to the tissue being treated. Looked at in a different way, the surgeon can apply the required power level from the start, with much reduced danger of electrode damage or unwanted tissue disruption.

The electrode identification circuit will now be described in more detail with reference to FIGS. 2 and 3.

The electrode identification circuit 50 is centred on an operational amplifier 52 having a low impedance output 52A driving an excitation primary winding 54A of an isolation transformer 54. A secondary winding 54S of the transformer 54 is coupled across the input leads 50A and 50B of the circuit 50 so that winding 54S and capacitor 34 of the electrode assembly form a parallel resonant circuit. The resonant frequency of the resonant circuit is typically within the range of from 2 kHz to 150 kHz, depending on the value of capacitor 34.

The transformer 54 also has a sense winding 54B coupled between an AC ground on one side and the inverting input 52I of the operational amplifier 52, thereby providing a feedback path from the transformer. Since winding 54B is effectively coupled to the excitation winding 54A via the resonant secondary winding 54S, the presence of the resonant circuit largely filters out the harmonics of the square wave output of the operational amplifier 52.

Clamp diodes D1 and D2 connected with opposite pluralities across sense winding 54B provide, in conjunction with capacitor C3 and resistor R4, a phase shift network causing a 90 degree phase lag with respect to the excitation winding output. The diodes also provide protection against excessive radio frequency voltages received from the generator radio frequency output applied via conductors 38A and 38B.

The three windings 54A, 54B and 54S of transformer 54 are wound on a three-section bobbin with a central threaded iron dust core 54C, this material being chosen due to its high curie point and consequent minimal thermal drift. Alternatively, core 54C may be made of a ferrite material with a comparatively large A1 value in conjunction with a calibration reference to allow compensation for thermal drift by, for example, switching in a known capacitance across the resonant winding 54S.

Coupling between the resonant secondary winding 54S and the other windings 54A, 54B of the transformer 54 is comparatively low to limit radio frequency feedback. Typically, the leakage inductance is in the region of 3 mH.

It will be appreciated from the above that operational amplifier 52 acts as an oscillator, oscillating at the resonant frequency of the resonant circuit produced by secondary winding 54S and capacitor 34. The output signal produced by the operational amplifier 52 is amplified in a buffer amplifier 56 and applied to output terminal 50C from where it is fed to the controller 48 (see FIG. 1). Controller 48 contains a counter for determining the frequency of oscillation or an equivalent measurement from which the identity of the electrode assembly is obtained.

As a safety feature the controller 48 includes means for determining from the output of the identification circuit 50 whether any electrode assembly is connected to the handpiece 12. In such an eventuality, the oscillation frequency of the circuit 50 is outside a predetermined range (in this embodiment it is higher than 150 kHz) and the adjusting means generates a signal indicative of no electrode assembly being connected and the supply of RF output power to the handpiece 12 is inhibited.

Figure 2:
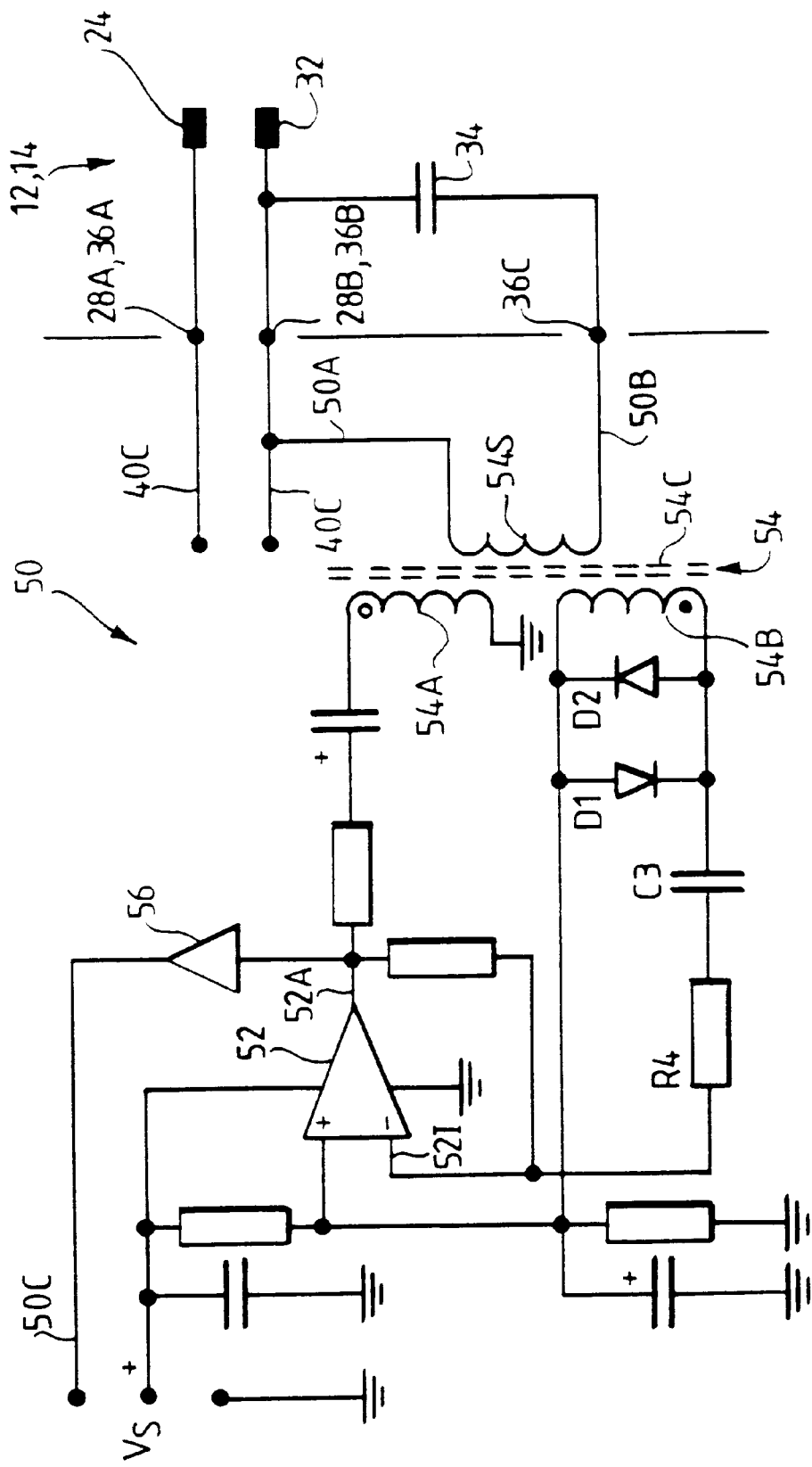
FIG. 2 is an electrical circuit diagram of an electrode assembly and an identification circuit, the latter forming part of the generator of FIG. 1.
Figure 3:
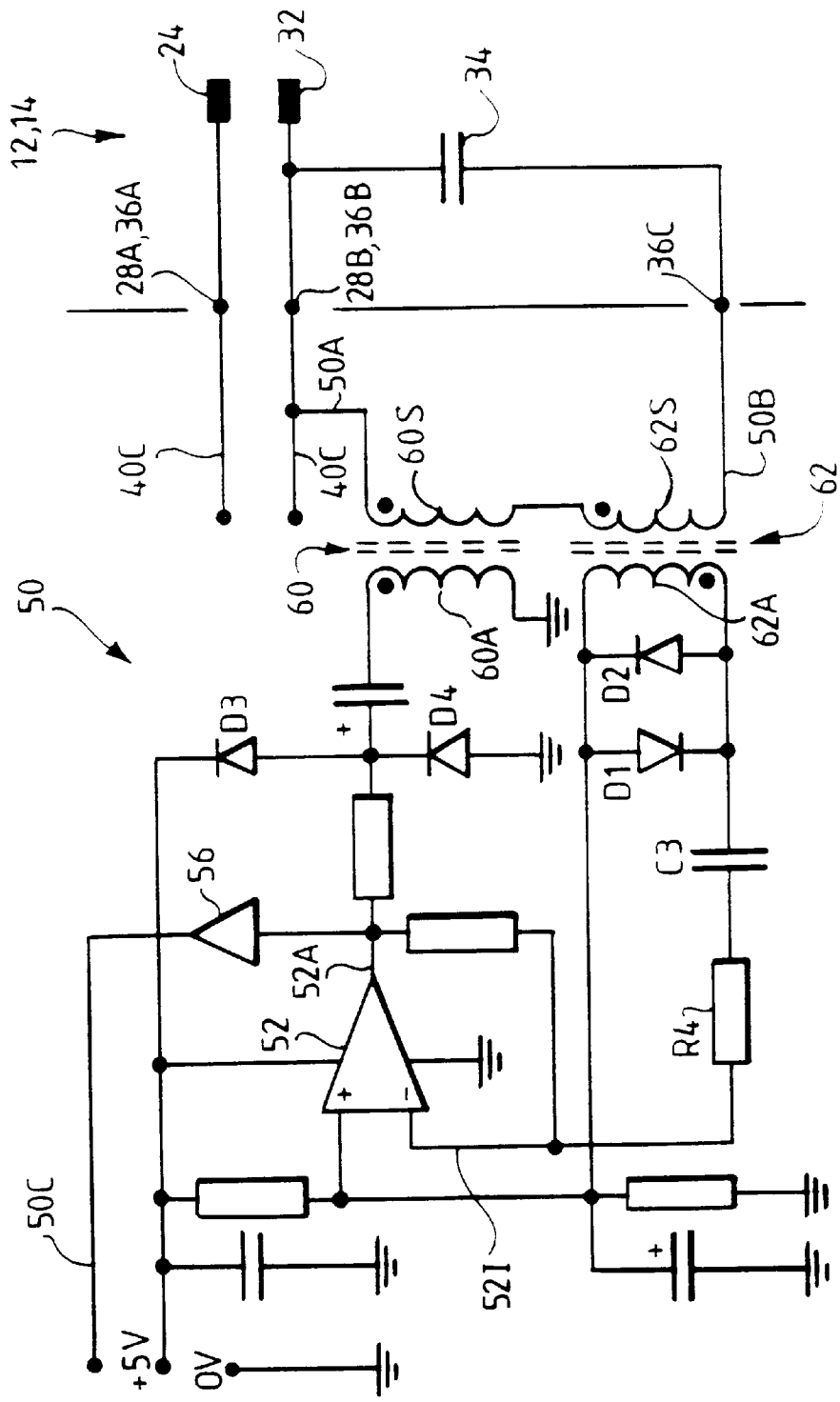
FIG. 3 is an electrical circuit diagram showing the electrode assembly and an alternative identification circuit.

In an alternative embodiment, shown in FIG. 3, the electrode identification circuit 50 has two isolation transformers 60 and 62 to avoid magnetic coupling between an excitation winding 60A coupled to the operational amplifier output 52A on the one hand, and a sense winding 62A coupled to the non-inverting input 52I of the operational amplifier on the other hand. Secondary windings 60S and 62S of the two transformers are coupled in series, their combined inductance forming a parallel resonant circuit with electrode assembly capacitor 34. Compared with the circuit of FIG. 2, the lack of magnetic coupling as a result of the dual transformer arrangement reduces the transmission of harmonics to the feedback loop of the oscillator. Thus all energy supplied into excitation winding 60A is filtered in such a way that only filtered energy arrives at the sense winding 62A.

In this embodiment, two additional diodes D3 and D4 are used to clamp and protect the operational amplifier 52 from inadvertent radio frequency inputs on the third conductor 50B (e.g. by misuse of the electrode assembly and handpiece or due to insulation failure).

In other respects, the identification circuit of FIG. 3 corresponds to that of FIG. 2.

In the above detailed description we have used the example of an electrosurgical instrument intended for urological procedures, in particular cystoscopic procedures. The invention is equally applicable to electrosurgical instruments in other fields, such as hysteroscopic and arthroscopic procedures.

Parts of an instrument for hysteroscopic use are shown in FIG. 4. In this case, an electrode assembly 14 (which may have an electrode configuration similar to that shown in FIG. 1A) has a plug section 18 and housing 33 very similar to the corresponding parts of the urological instrument of FIG. 1. As in the urological instrument, a capacitor 34 (here shown by dotted lines) is positioned in a laterally projecting key portion 33K of the housing 33 to contact a spring-loaded contact similar to contact 36C of FIG. 1 in a connector unit 70 attached to cable 20.

Connector unit 70 is typically attached to the outside of an endoscope (not shown).

Referring to FIG. 5, an arthroscopic instrument has a handpiece 12 ergonomically designed to aid tissue manipulation. With regard to the interengagement of the handpiece 12 and electrode assembly 14, these parts have features similar to the features described with reference to the urological instrument of FIG. 1.

It will be seen by comparing the electrode assemblies 14 and handpieces 12 and connector unit 70 of the instruments shown in FIGS. 1, 4, and 5, that the respective plug sections 18 are of different lengths. In each case, the receptacle 35 has contacts 36A and 36B for engaging contacts 28A and 28B of the plug section 18 which are located according to the length of the corresponding electrode assembly plug section 18. These differences are shown more clearly in FIGS. 6A, 6B, and 6C which show the urological, hysteroscopic, and arthroscopic electrode assemblies respectively. In all three figures, the spring-loaded contact 36C for engaging the terminal of the capacitor 34 is also shown. Furthermore, in FIGS. 6B and 6C a stop 74 is shown diagrammatically. This is for limiting insertion of plug section 18 and, in practice, is typically provided in those instruments by means of a transversely oriented dowel in the receptacle 35.

Figure 6A:
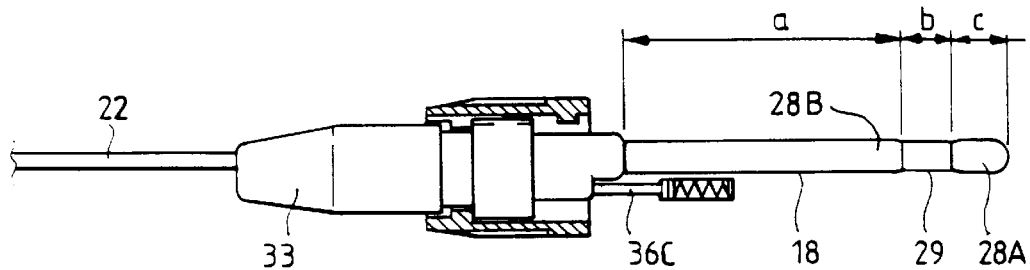
FIGS. 6A, 6B, and 6C are fragmentary side elevations of the electrode assemblies of the urological, hysteroscopic, and arthroscopic instruments of FIGS. 1, 4, and 5 respectively, showing the differences between the plug sections of these assemblies.
Figure 6B:
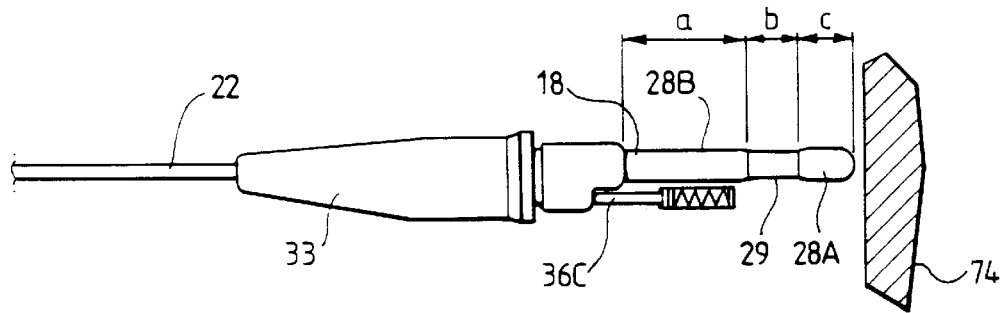
Figure 6C:
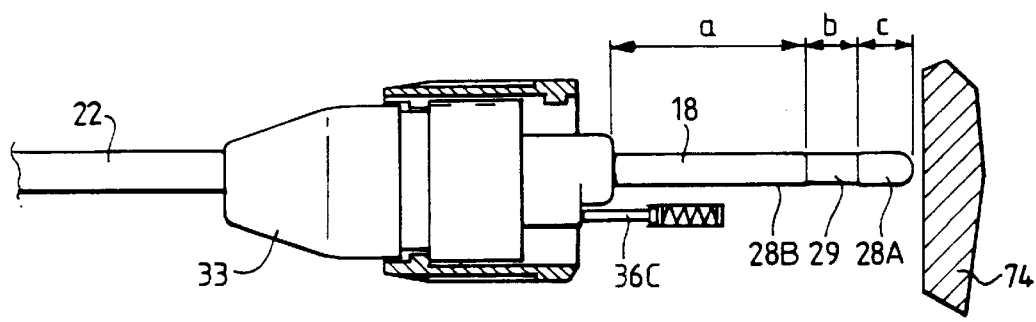

It will be noted that although the lengths c and b of the contact 28A at the end of the plug unit 18, and the insulative spacer 29 remain the same in all three embodiments, the distance a between the housing 33 and the insulative spacer 29 is different in each case. The same dimensions are maintained in all electrode assemblies within each speciality group. Thus, all electrode assemblies intended for urological procedures have a relatively long plug section 18, all electrode assemblies for hysteroscopic procedures have a short plug section 18, while all those intended for arthroscopic procedures have a medium length plug section 18, as shown in FIGS. 6A, 6B, and 6C. Consequently, each electrode assembly can only be used with a handpiece 12 or connector unit 70 intended for the same speciality group. If there is a mismatch in the mechanical interface between an electrode assembly and a handpiece or connector unit, electrosurgical power cannot be supplied from the generator to the electrodes either because one or both of the contacts 28A, 28B fails to make contact with a corresponding contact in the handpiece or connector unit, or because the spring-loaded contact 36C does not engage with the identification capacitor 34 in the housing 33.

By providing similar interface restrictions at the connector 21 (see FIG. 1), it can be ensured that each electrode assembly can only be used with a generator output connection configured for the speciality group of the electrode assembly. As a result, it is possible to set up the generator differently according to speciality grouping, and so that it responds differently to the various identification capacitor values within the range of electrode assemblies for that speciality grouping. This means that a wider range of generator settings is available than would be possible by relying entirely on a limited range of values for capacitor 34.

What is claimed is:

1. An electrosurgical instrument comprising:

a first unit including a generator for generating radio frequency power, and a second unit including an electrode assembly, the second unit being detachably connectible to the first unit such that radio frequency power can be conveyed to the elctrode assembly, wherein the second unit includes a passive electrical identification component having a parameter of a finite non-zero value indicative of a characteristic of the electrode assembly, and the first unit includes a sensing circuit including a second passive electrical component and an oscillator, the second component forming a resonant circuit with the identification component when the second unit is connected to the first unit and the oscillator oscillating at the resonant circuit's resonant frequency, the sensing circuit generating an output signal based on the oscillator's oscillating frequency and being representative of the parameter value, the first unit further including a controller connected to the sensing circuit and receiving the output signal, the controller being configured to adjust the output of the generator in response to the output signal from the sensing circuit so as to suit the indicated electrode assembly characteristic.

2. An instrument according to claim 1, wherein the parameter is electrical impedance, and wherein the sensing circuit produces an electrical output signal which is dependent on the impedance of the identification component.

3. An instrument according to claim 1, wherein the sensing circuit's second component is a reactive component which forms the resonant circuit with the identification component when the second unit is connected to the first unit, the resonant frequency of the resonant circuitry being dependent on the reactance of the identification component.

4. An instrument according to claim 3, wherein the identification component is a reactive component and the oscillator's frequency of operation is dependent on the reactance of the identification component.

5. An instrument according to claim 3, wherein:
the identification component is a capacitor and the reactance component comprises a first winding of a transformer,
the capacitor is connected between a first pair of contacts on the second unit, and
the transformer first winding is connected between a second pair of contacts on the first unit,
the first and second pairs of contacts being so located that the contacts of one pair engage respective contacts of the other pair when the first unit is connected to the second unit to form the said resonant circuit.

6. An instrument according to claim 5, wherein the transformer is an isolation transformer and has a second winding forming part of the oscillator.

7. An instrument according to claim 6, wherein the transformer has a third winding coupled to an oscillating device of the oscillator and acting as a resonant circuit excitation winding.

8. An instrument according to claim 6, including a second transformer having a first winding coupled to an oscillating device of the oscillator and acting as a resonant circuit excitation winding, and a second winding coupled in series in the resonant circuit.

9. An instrument according to claim 5, wherein one of the contacts of each of the first and second pairs also serves as a contact for conducting radio frequency electrosurgery currents between the generator and the electrode assembly.

10. An instrument according to claim 2, wherein the identification component is a capacitor the capacitance value of which is indicative of the electrode assembly characteristic.

11. An instrument according to claim 2, wherein first unit comprises the generator, a connector, and a cable for coupling the generator to the connector, the cable including conductors for coupling the identification component to the sensing circuit, and wherein the second unit is in the form of an electrode assembly including a connector which mates with said connector of the first unit.

12. An instrument according to claim 11, wherein said connector of the first unit is integrated in a handpiece of the instrument.

13. An instrument according to claim 1, wherein:
the sensing circuit is configured to detect a plurality of different values of said parameter, and
the controller is configured to set the output power of the generator according to the output signal provided by the sensing circuit and representative of the identification component parameter.

14. An instrument according to claim 13, wherein the controller is operable to adjust the average supply voltage supplied to a radio frequency output circuit of the generator in response to the output signal of the sensing circuit.

15. An instrument according to claim 14, wherein the generator includes a switched mode power supply, and the controller is coupled to the power supply and operable to adjust the duty cycle of the switched output in response to the output signal of the sensing circuit.

16. An instrument according to claim 1, wherein the controller includes a circuit for setting a generator output voltage limit for tissue vaporisation, the limit being determined according to the identification component property.

17. An electrode assembly for an electrosurgical instrument comprising:
at least one electrode,
a mounting portion for detachably securing the assembly to an another part of the instrument, and
a passive electrical identification component arranged to form a resonant circuit with a reactive component in a sensing circuit associated with said other part of the instrument, the sensing circuit including an oscillator oscillating at the resonant circuit's resonant frequency, the identification element having a parameter of a finite non-zero value indicative of the assembly.

18. An electrode assembly according to claim 17, wherein the parameter is electrical impedance.

19. An electrode assembly according to claim 18, wherein the identification component is a capacitor, the capacitance value of which is indicative of the assembly, and wherein the mounting portion includes a pair of electrical contacts arranged to engage electrical contacts in the said other part of the instrument's handpiece, the capacitor being connected between the contacts of the assembly.

20. An electrode assembly according to claim 17, wherein the electrode assembly is for use in a conductive liquid and has a first, active electrode at an extreme distal end of the assembly and a second, return electrode spaced proximally from the active electrode.

21. An electrosurgical generator for use with a plurality of different electrode assemblies including respective electrical identification components having different finite non-zero parameter values indicative of the characteristics of the electrode assemblies, wherein the generator includes
a sensing circuit configured to include a reactive component which forms a resonant circuit with an electrode assembly's respective electrical identification component when the electrode assembly is connected to the generator and an oscillator oscillating at the resonant circuit's resonant frequency, the sensing circuit generating a signal based on the oscillator's oscillating frequency and being representative of the parameter values, and
a controller connected to the sensing circuit and receiving the output signal, the controller being configured to adjust the output of the generator in response to the output signal according to the indicated characteristic of an electrode assembly connected to the generator.

22. A generator according to claim 21, wherein the sensing circuit is configured to produce an electrical output signal the nature of which is dependent on the impedance of an identification component in the form of a passive electrical component.

23. A generator according to claim 22, wherein the controller is arranged to set at least one of the output power of the generator and a maximum peak output voltage.

24. A method of assembling and operating an electrosurgical instrument comprising:
providing a first unit including an oscillator, a reactive component and an electrosurgical generator for generating radio frequency power;
providing a plurality of second units comprising different electrode assemblies each having means for detachable mounting to the first unit and each including an electrical identification component having a parameter of a finite non-zero value indicative of a characteristic of the respective assembly;

selecting one of the second units and mounting it to the first unit thereby causing the identification component and reactive component to form a resonant circuit and the oscillator to oscillate at the resonant circuit's resonant frequency, and in the first unit, sensing the oscillator's oscillating frequency and thereby the said identification component parameter value and automatically adjusting the generator output in response to said sensing to suit the characteristic of the electrode assembly of the selected second unit.

25. A method according to claim 24, wherein the generator nominal output power is automatically adjusted according to the sensed identification parameter value.

26. A method according to claim 24, wherein a tissue vaporisation limit voltage is automatically adjusted according to the sensed identification parameter value.

27. A method according to claim 24, wherein a characteristic of the generator output is adjusted in response to the identification component parameter value according to the category of surgical procedure as characterised by the mechanical configuration of the generator output connector to which the electrode assembly is connected.

28. A kit of parts for assembling an electrosurgical instrument, comprising a first unit including an electrosurgical generator for generating a radio frequency electrosurgical voltage, and a plurality of different second units including different electrode assemblies, each second unit including means for mounting to the first unit, wherein each second unit includes an electrical identification component having a parameter of a respective value selected from a range of finite non-zero values and indicative of a characteristic of the respective electrode assembly, and the first unit includes means for sensing the indicating parameter when a second unit is mounted to the first unit, said sensing means including a second electrical component forming a resonant circuit with the respective identification component of a second unit mounted to the first unit and an oscillator oscillating at the resonant circuit's resonant frequency, the generator including adjustment means responsive to an output signal from the sensing means based on the oscillator's oscillating frequency to adjust the output of the generator, whereby the generator output is automatically adjusted to suit the different characteristics of the electrode assemblies of the second units when they are selectively mounted to the housing according to the sensed parameter value.

29. A kit of parts according to claim 28, wherein the first unit comprises the generator, a connector, and a cable for coupling the generator to the cable, and wherein each second unit comprises a said electrode assembly which itself includes a connector for mating with said connector of the first unit.

30. An electrosurgical instrument comprising a first unit including a generator for generating radio frequency power, and a second unit including an electrode assembly, the second unit being detachably connectible to the first unit such that radio frequency power can be conveyed to the electrode assembly, wherein the second unit includes a passive electrical identification component having a parameter of a finite non-zero value indicative of a characteristic of the electrode assembly, and the first unit includes a sensing circuit responsive to the identification component when the second unit is connected to the first unit, the sensing circuit generating an output signal representative of the parameter value, the first unit further including a controller connected to the sensing circuit and receiving the output signal, the controller being configured to adjust the output of the generator in response to the output signal from the sensing circuit so as to suit the indicated electrode assembly characteristic, the sensing circuit including a reactive component which forms a resonant circuit with the identification component when the second unit is connected to the first unit, the resonant frequency of the resonant circuitry being dependent on the reactance of the identification component;

wherein the identification component is a capacitor and the reactance component comprises a first winding of a transformer, the capacitor being connected between a first pair of contacts on the second unit, and the transformer first winding being connected between a second pair of contacts on the first unit, and the first and second pairs of contacts being so located that the contacts of one pair engage respective contacts of the other pair when the first unit is connected to the second unit to form the said resonant circuit.

31. An instrument according to claim 30, wherein the transformer is an isolation transformer and has a second winding forming part of the oscillator.

32. An instrument according to claim 31, wherein the transformer has a third winding coupled to an oscillating device of the oscillator and acting as a resonant circuit excitation winding.

33. An instrument according to claim 31, including a second transformer having a first winding coupled to an oscillating device of the oscillator and acting as a resonant circuit excitation winding, and a second winding coupled in series in the resonant circuit.

34. An instrument according to claim 30, wherein one of the contacts of each of the first and second pairs also serves as a contact for conducting radio frequency electrosurgery currents between the generator and the electrode assembly.

35. An electrosurgical instrument comprising a first unit including a generator for generating radio frequency power, and a second unit including an electrode assembly, the second unit being detachably connectible to the first unit such that radio frequency power can be conveyed to the electrode assembly, wherein the second unit includes a passive electrical identification component having a parameter of a finite non-zero value indicative of a characteristic of the electrode assembly, and the first unit includes a sensing circuit responsive to the identification component when the second unit is connected to the first unit, the sensing circuit generating an output signal representative of the parameter value, the first unit further including a controller connected to the sensing circuit and receiving the output signal, the controller being configured to adjust the output of the generator in response to the output signal from the sensing circuit so as to suit the indicated electrode assembly characteristic, wherein the sensing circuit is configured to detect a plurality of different values of said parameter, and the controller is configured to set the output power of the generator according to the output signal provided by the sensing circuit and representative of the identification component parameter, the controller being operable to adjust the average supply voltage supplied to a radio frequency output circuit of the generator in response to the output signal of the sensing circuit, and wherein the generator includes a switched mode power supply, and the controller is coupled to the power supply and operable to adjust the duty cycle of the switched output in response to the output signal of the sensing circuit.

* * * * *